US005874549A

United States Patent [19]
Hadley

[11] Patent Number: 5,874,549

[45] Date of Patent: Feb. 23, 1999

[54] ACID-CLEAVABLE COMPOUND

[75] Inventor: Stephen Hadley, Seattle, Wash.

[73] Assignee: NeoRx Corporation, Seattle, Wash.

[21] Appl. No.: 118,578

[22] Filed: Sep. 9, 1993

Related U.S. Application Data

[63] Continuation of Ser. No. 589,579, Sep. 28, 1990, abandoned.

[51] Int. Cl.[6] ........................ C07H 15/24; C07D 403/00; C07D 337/00; C07C 233/00

[52] U.S. Cl. ........................... 536/6.4; 530/300; 530/350; 540/476; 540/576; 549/9; 564/123

[58] Field of Search .................................... 530/300, 350; 548/900; 540/476, 576; 536/6.4; 549/9; 564/123

[56] References Cited

U.S. PATENT DOCUMENTS

| | | | |
|---|---|---|---|
| 4,569,789 | 2/1986 | Blattles et al. | 260/112 R |
| 4,975,278 | 12/1990 | Lenter et al. | 424/94.3 |
| 5,017,693 | 5/1991 | Hylarides et al. | 530/390 |

OTHER PUBLICATIONS

Jerry March, *Advanced Organic Chemistry,* Third Edition, John Wiley & Sons, 1985, New York, pp. 745–758.

I. Pastan and M.C. Willingham, "The Pathway of Endocytosis," in I. Pastan and M.C. Willingham (ed.), *Endocytosis,* Plenum Press, New York and London, 1985, pp. 1–44.

Biochemistry 1989; 18; pp. 2501–2509; "New Protein Cross–Linking Reagents that are Cleaved by Mild Acid"; Srinivasachar et al.

J. Org. Chem. Soc. 1988, 53, 4130–5139; "Prodrugs Based on Masked Lactones. Cyclization of τ–Hydroxy Amides"; Johnson et al.

J. Amer. Chem. Soc. 1988, 110, 6794–6796; "Fast Hydrolysis of an Aliphatic Amide at Neutral pH and Ambient Temperature. A Peptidase Model"; Menger et al.

Biochemistry 1985, 24, 1517–1524; New Heterobifunctional Protein Cross–Linking Reagent that forms an Acid–Labile Link; Blättler et al.

Cancer Research 49, 4373–4384; Aug. 15, 1989; "Acid pH in Tumors and its Potential for Therapeutic Exploitation"; Ian F. Tannock et al.

*Primary Examiner*—Elli Peselev
*Attorney, Agent, or Firm*—Seed and Berry LLP

[57] ABSTRACT

A bicyclic, non-aromatic hydrocarbon compound, optionally having one or more N, O or S atoms in the bicyclic skeleton, and having as substituents an acid group and an amido group, which are vicinal and in a syn-position, wherein the amido group is not anilido and the acid group is carboxyl or carboxyl in a form metabolizable to a free carboxyl group, and wherein said bicyclic skeleton is optionally unsaturated, except in the bond between said groups, acid-cleavably links an amide-containing active agent to a targeting agent, which is linked by a linker arm to the bicyclic skeleton.

13 Claims, 9 Drawing Sheets

1

2 3

4 5

6

4 7

8

9 10 11 12 13 14

14 or MAb-IT-S

6 n=1
15 n=2
16 n=3

17

ACID-CLEAVABLE COMPOUND

CROSS-REFERENCE TO RELATED APPLICATION

This application is a continuation of U.S. patent application Ser. No. 07/589,579, filed Sept. 28, 1990, now abandoned.

BACKGROUND OF THE INVENTION

This invention relates to compounds containing a cleavable linker between a deliverable compound, e.g., a pharmaceutical agent, and a targeting moiety, e.g., a protein.

There are many diagnostic and therapeutic agents which suffer from non-selectivity of effect. Thus, cells not in need of a particular treatment are nevertheless exposed to the treating agent. Analogously, cells not intended to be the subject of a diagnosis, e.g., an imaging procedure such as radioimaging or MRI, are nevertheless subjected thereto, i.e., are imaged. As a result of this pervasive non-selectivity problem, much effort has been expended to enhance the selectivity of such pharmaceutical agents.

One technique often used is the binding of the non-selective pharmaceutical agent to another chemical moiety which is capable of targeting the resultant conjugate to a desired site. In most cases, the conjugate must also provide a means for cleaving the "active" agent from the targeting portion. This combination of features poses a unique biochemical problem: Not only must the conjugate provide a targeting moiety specific for a given site, but the cleavability must also be functional at that site and in such a manner that the agent retains its therapeutic or diagnostic capabilities.

In one general method, a protein such as a monoclonal antibody is attached to the pharmaceutical agent. The antibody is selected to be specific for the type of cells desired to be treated or diagnosed. The targeting portion has been attached to the pharmaceutical agent by a variety of linking groups, some of which are cleavable linkers.

The concept of selectively cleavable linkers has been proposed as a method to deliver free active drugs (as well as imaging agents) to tumors using antibody carriers. The method utilizes the ability of antibodies to localize and bind to tumor cells in vivo, due to the presence of tumor-specific antigens on the surface of many tumor cells. By coupling these tumor-specific antibodies to tumor-treating drugs via a selectively cleavable linker which is cleaved upon localization of the complex, releasing the free drug, the drug can be delivered specifically to the tumor cells, thereby reducing the side-effects of the often toxic tumor-treating drugs. One goal of the development of such selectively cleavable linkers is to provide a mechanism by which the drug is delivered free of any covalent modification, which may be critical since such modification may render the drug biologically inactive.

One physiological parameter which can be exploited for selective linker cleavage at the tumor site is pH. It has been reported that the pH of the extracellular fluid surrounding the tumor cells inside solid tumor masses is acidic (Tannock, I. F. et al., Cancer Research 49, 4373–4384 (1989)). In addition to extracellular pH, receptor mediated endocytosis of the antibody conjugate by a tumor cell followed by fusion of the endosome with a lysosome exposes the conjugate to an acidic pH of 4.5–5.0 (see, e.g., "The Pathway of Endocytosis, Pastan, I. and Willingham, M. C. in *Endocytosis*, I. Pastan and M. C. Willingham, eds. Plenum, N.Y. (1985)).

One of the more useful functional groups for derivatization by a linking reagent and which is available on some drugs, including, for example, the anticancer agents daunomycin and doxarubicin, is the amino group. One of the common methods to derivatize an amino group is to react it with a carboxylic acid group to form an amide bond.

However, typical amide bonds are notoriously resistant to non-enzymatic hydrolysis at acid pH. Harsh reaction conditions such as refluxing in concentrated aqueous acid for several hours to effect hydrolysis are not uncommon. On the other hand, certain amides have been shown to undergo facile hydrolysis under mildly acidic conditions. For example, the amide bond of maleamic acids (See Table 1) has been shown to be quite labile at pH 4.5 (See, e.g., Kirby, A. J. et al., J. Chem. Soc. Perkin II, 1206–1214 (1972) and Aldersley, M. F. et al., J. Chem. Soc. Perkin II, 1487–1495 (1974)). It has also been shown that by modifying the $R_a$ and $R_b$ groups, the rate of hydrolysis of the amide group can be substantially changed (Kirby and Aldersley, supra.). This relationship between structure and activity is summarized in Table 1:

TABLE 1

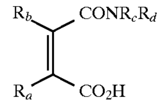

| Cpd | $R_a$ | $R_b$ | $R_c$, $R_d$ | Relative Rate* |
|---|---|---|---|---|
| 1 | H | H | Me, H | 1 |
| 2 | Me | H | Me, H | 31.2 |
| 3 | Et | H | Me, H | 32.8 |
| 4 | iPr | H | Me, H | 44.5 |
| 5 | tBu | H | Me, H | 68.0 |
| 6 | Me | Me | nPr, H | $2.35 \times 10^4$ |
| 7 | $-(CH_2)_4-$ | | Me, H | 540 |
| 8 | $-(CH_2)_3-$ | | Me, H | $4.2 \times 10^{-5}$ |
| 9 | $-(CH_2)_2-$ | | Me, H | $4.2 \times 10^{-6}$ |
| 10 | $-CH=CH-CH=CH-$ | | Me, H | 0.72 |
| 11 | H | H | iPr, H | 0.7 |
| 12 | H | H | tBu, H | 2.6 |
| 13 | H | H | Ph, H | 4.5 |
| 14 | H | H | Me, Me | 42.7 |
| N-methyl acrylamide ($CH_2CHCONHMe$) | | | | $1.4 \times 10^{-7}$ (est.) |

U.S. Pat. No. 4,569,789 (Blattler et al.) discloses the use of maleamic acids as acid-cleavable linkers. The linkers are formed by reacting the amine-containing compound with the maleamic acid portion of a linker which also contains a group which can react with a sulfur-containing group of a protein. These linkers are disclosed in the patent and the corresponding publication (Biochem. 24, 1517–1524 (1985)) as having a $T_{1/2}$ for hydrolysis of the acid-cleavable bond of approximately 8 hr at pH 4.0. Unfortunately, a pH of 4.0 is at the lower end of the pH ranges most often cited in the literature for lysosomes and extracellular fluid surrounding tumor cells. Thus, the art still lacks an acid-cleavable linker which hydrolyzes at a physiologically more useful pH, e.g., 5.0–5.5, with a preferred $T_{1/2}$ of 8 hr or, preferably, less.

SUMMARY OF THE INVENTION

One aspect of this invention provides a bicyclic, non-aromatic hydrocarbon compound, optionally having one or more N, O or S atoms in the bicyclic skeleton, and having as substituents an acid group and an amido group, which are vicinal and in a syn-position, wherein the amido group is not anilido and the acid group is carboxyl or carboxyl in a form metabolizable to a free carboxyl group, and wherein said bicyclic skeleton is optionally unsaturated, except in the bond between said groups. In a preferred embodiment, the amido group is acid cleavable, and the amino group from which the amido group is derived is from a therapeutic or diagnostic active agent. In a particularly preferred embodiment, the bicyclic compound has the formula

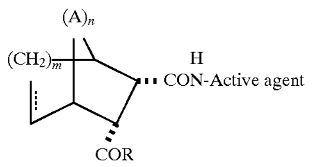

wherein

A is —$CH_2$—, —O—, —S— or >N—$C_{1-6}$-alkyl, wherein n is 1, 2 or 3, when A is —$CH_2$—, or n is 1 when A is —O—, —S— or >N—$C_{1-6}$-alkyl;

m is 1 or 2;

-------- is a single or double bond; and

R is OH, $OR_1$ or $SR_1$, wherein $R_1$ is an ester moiety.

Also particularly preferred is an embodiment wherein the amido group can be released under mild acidic conditions of pH≧5.0 with a $T_{1/2}$ of about 8 hours or less.

Another aspect of this invention provides a bicyclic compound as described above, wherein the bicyclic ring is further substituted by a linker arm having a reactive group effective for linking to a polypeptide or other targeting agent, and wherein the reactive group on the linker arm is covalently linked to a targeting agent. In a particularly preferred embodiment, the targeting agent is an antibody, an antibody fragment, or a ligand for a cell-surface receptor.

A third aspect of this invention provides a method of linking a physiological targeting agent to an active agent, wherein said active agent is linked to the targeting agent through an acid-cleavable linker, the improvement wherein the linker comprises a saturated or unsaturated, non-aromatic bicyclic skeleton having as substituents an acid group and an acid-cleavable amido group, which are vicinal and in a syn-position, wherein the amido group is a reaction product of an amine group from the therapeutic or diagnostic agent and the acid group is carboxyl or carboxyl in a form metabolizable to a free carboxyl group. In a preferred embodiment, the acid-cleavable amido bond is hydrolyzed under mild acidic conditions of pH≧5.0 with a $T_{1/2}$ of about 8 hours or less.

A fourth aspect of this invention provides a method of in vivo-administering an active agent preferentially to a desired acidic site comprising administering said agent in the form of a bicyclic compound as described above, wherein the targeting moiety is selective for said site.

Yet another aspect of this invention provides a support material having a targeting agent linked thereto by an acid-cleavable linker comprising a support material having an attachment group attached thereto which group is covalently linked to an acid-cleavable linker, wherein said linker comprises a bicyclic non-aromatic hydrocarbon compound, optionally having one or more N, O or S atoms in the bicyclic skeleton, and having as substituents an acid group and an amido group which are vicinal and in a syn-position, wherein the acid group is carboxyl or carboxyl in a form metabolizable to a free carboxyl group, said bicyclic skeleton is optionally unsaturated except in the bond between said acid and amido groups, the amido group is acid-cleavable, the bicyclic ring is further substituted by a linker arm having a reactive group which is covalently linked to the targeting agent or to the attachment group of the support material, and the amido group is derived from the targeting agent when the reactive group on the linker arm is covalently linked to the attachment group of the support material, and is derived from the attachment group of the support material when the reactive group on the linker arm is covalently linked to the targeting agent, as well as a method of using said support material to isolate a substance having a group which selectively binds to a targeting agent. In a preferred embodiment, the targeting agent binds to a cell-surface receptor, and the substance to be isolated is a cell of a particular type having said receptor, and which cell is present in a mixture of cells of various types.

BRIEF DESCRIPTION OF THE DRAWINGS

Various other objects, features and attendant advantages of the present invention will be more fully appreciated as the same becomes better understood when considered in conjunction with the accompanying drawings, and wherein.

Figure 1:
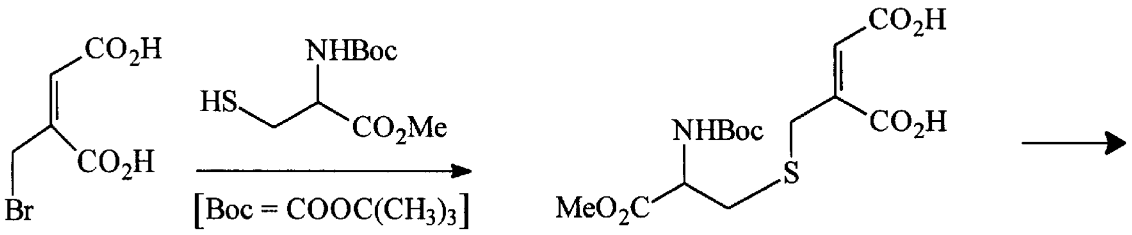
FIG. 1 outlines the reaction pathway described in Example 1.
Figure 1:
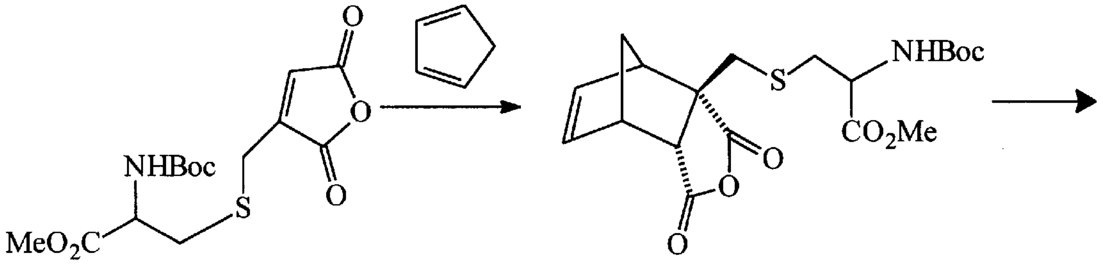
Figure 1:
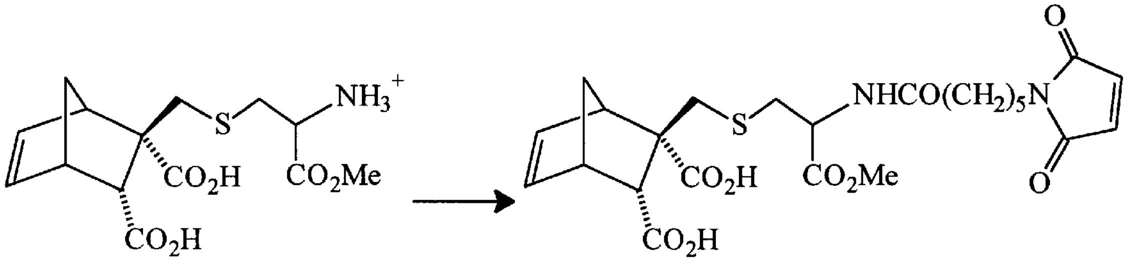
Figure 1:
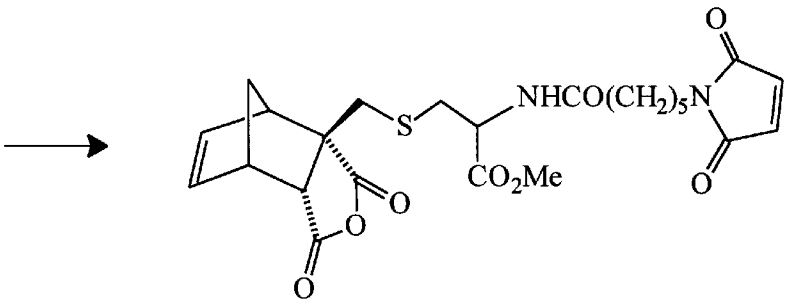

By "bicyclic" is meant bridged bicyclic rings; by definition, these are rings which are fused through nonadjacent atoms. Preferred bicyclic groups of this invention have, for example, 7–10 carbon atoms or the equivalent, e.g., a saturated or unsaturated norbornane skeleton. By equivalent is meant, for example, that one or more of the carbon atoms may be substituted by oxygen, sulfur or N—$C_{1-6}$-alkyl; in particular a carbon atom in the methylene bridge, particularly where n=1, can be substituted by, e.g., O, S or N—$CH_3$.

When the fundamental properties, e.g., rigidity of the bicyclic compounds of this invention, are not changed by substitutions which produce one or more additional rings, such polycyclic compounds are also equivalents; i.e., they are bicyclic rings containing further rings.

Saturated bicyclic skeletons are preferred, as carboxyl groups which are attached to such skeletons generally have higher $pK_a$s than those of the corresponding carboxyl groups attached to unsaturated carbon atoms on unsaturated bicyclic skeletons. However, unsaturated bicyclic skeletons, except those unsaturated in the double bond between the acid and amido groups, are also suitable, e.g., those containing a 5,6-double bond or the equivalent bond, e.g., in a [2.3.1] ring. Furthermore, the skeleton may contain additional substituents which modify the $PK_a$ of the carboxylic acid to a preferred range for a particular purpose, or which contribute other effects such as, e.g., increased solubility of the linker.

By "vicinal and in a syn-position" is meant that the named substituents are located on adjacent ring atoms in the bicyclic ring, and are on the same side of the (nominal) plane of the ring; i.e., both substituents must be either above the plane or below it. This configuration is analogous to substituents which are cis to each other with respect to a double bond.

Suitable amido groups are preferably the reaction product of a carboxyl group (including the carboxyl group generated during the reaction of such an amino group with an anhydride) with a primary amino group which is attached to an active agent; however, in addition, any other nitrogen-containing group which is reactive with a carboxyl group to form an acid-cleavable bond is suitable, e.g., a mono-N-substituted amino group, or other group such as, e.g., a hydrazine group.

By "carboxyl or carboxyl in a form or metabolizable to a free carboxyl group" as used herein is meant, for example, a group of the formula —COR, wherein R is an ester, a thioester, or any other group which is easily metabolizable to an OH group in vivo, e.g., after administration to a human and before in vivo cleavage of the amido group which releases the active agent. Suitable ester and thioester groups include O(S)—$C_{1-6}$-alkyl. R can also include amide groups which are metabolized faster than the cleavage of the amido group which yields the active agent.

By acid-cleavable as used herein is meant that the amide bond between the linker and the active agent which is to be released as a free amine group is cleaved at a pH below 7.0, preferably at a pH below 6.0, and most preferably at a pH between 4.5 and 5.0, preferably at a temperature of 37° C., and preferably under physiological conditions. In a most preferred embodiment, this cleavage will occur under physiological conditions within the targeted tissue with a $T_{1/2}$ of at most about 8 hours, and most preferably less than 4 hours. In a further preferred embodiment, the amide bond will be cleaved at a differentially higher rate within a targeted tissue having a lower than normal pH, from the rate achieved in normal, untargeted tissue.

By active agent as used herein is meant an amino-group -containing compound which is of therapeutic, prophylactic, diagnostic or other value, and for which use it is necessary or preferred that the compound be delivered to a particular site within a patient's body. Examples of such compounds include drugs, cytotoxic agents, toxins, vaccines, diagnostics such as radio-labelled compounds, etc.

Suitable amine-containing active agents for linkage to the anhydride portion of the linker and subsequent hydrolysis and site-specific delivery include drugs for the treatment of a wide variety of disease states, such as, e.g., cancers, tumors, infections, inflammations, etc. In addition, the active agents may be other molecules whose site-specific delivery is preferred, e.g., recombinant nucleic acids for gene therapy or vaccines. Other active agents may include labelled molecules such as radiolabelled or paramagnetic molecules or atoms whose site-specific localization will aid in diagnosis or therapy. Other uses will be evident to one of ordinary skill in the art.

Exemplary cytotoxic active agents include toxins and drugs. Several of the native toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting substance. However, while elimination of the toxin B chain decreases non-specific cytotoxicity, it also generally leads to decreased potency of the toxin A chain-targeting substance conjugate, as compared to the corresponding holotoxin-targeting substance conjugate. However, all variations of administration of various toxin molecules are contemplated within the scope of this invention.

Within the present invention, preferred toxins include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides.

Exemplary drugs include amine-containing therapeutic compounds such as daunomycin, vinblastine, doxorubicin, bleomycin, methotrexate, 5-fluorouricil, 6-thioguanine, cytarabine and similar conventional therapeutics as described in *Cancer: Principles and Practice of Oncology,* 2d ed., V. T. DeVita et al., Chapter 14, Lippincott Co. Philadelphia, Pa, (1985). Experimental drugs will also be suitable for use within the present invention (see, e.g., *NCI Investigational Drugs, Pharmaceutical Data* 1987, NIH Publication No. 88–2141, Revised November 1987).

In addition to compounds having amino groups which themselves have therapeutic or diagnostic properties, the amino-containing compounds may be a chelating compound which is carrying some other active moiety, for example, a radioactive nuclide. Suitable chelating compounds are well known to those of skill in the art, and include those described in U.S. Ser. No. 07/373,426.

Preferred diagnostic and therapeutic radionuclides that may be either directly or indirectly attached to the linker group include gamma-emitters, positron-emitters, Auger electron-emitters, X-ray emitters and fluorescence-emitters, with beta- or alpha-emitters preferred therapeutic agents. Radionuclides are well-known in the art and include $^{123}I$, $^{125}I$, $^{130}I$, $^{133}I$, 135I, $^{47}Sc$, $^{72}As$, $^{72}Se$, $^{90}Y$, $^{88}Y$, $^{97}Ru$, $^{100}Pd$, $^{101m}Rh$, $^{119}Sb$, $^{128}Ba$, $^{197}Hg$, $^{211}At$, $^{212}Bi$, $^{212}Pb$, $^{109}Pd$, $^{11}In$, $^{67}Ga$, $^{68}Ga$, $^{67}Cu$, $^{75}Br$, $^{76}Br$, $^{77}Br$ $^{99m}Tc$, $^{11}C$, $^{13}N$, $^{15}O$ and $^{18}F$. Preferred therapeutic radionuclides include $^{188}Re$, $^{186}Re$, $^{203}Pb$ $^{212}Pb$ $^{212}Bi$ $^{109}Pd$ $^{64}Cu$, $^{67}Cu$ $^{90}Y$ $^{125}I$, $^{131}I$, $^{77}Br$, $^{211}At$, $^{97}Ru$, $^{105}Rh$, $^{198}Au$ and $^{199}Ag$.

In addition to amine-containing molecules (e.g., drugs) as noted above, the present invention is also directed to radiolabelled versions of these molecules.

By targeting agent is meant a compound which can be directed to a specific site, e.g., to a specific cell or tissue type, generally within a patient. In general, targeting agents are peptides or proteins, including antibodies or antibody fragments, including those derived from monoclonal antibodies. In addition, they may be ligands for cell-surface receptors, or receptors for cell-surface ligands. In a preferred embodiment, the targeting agent contains a free sulfhydryl group, or a compound which has a moiety which can be reduced to a free sulfhydryl group. In particular, for the purpose of this invention, this compound is a protein, and most particularly an antibody which is specific for the cell or tumor type which is intended to be treated or visualized.

Alternatively, the compound may be a haptan or other compound which is selectively bound by receptors on the surfaces of the cells or tissues which are targeted for delivery of the amine-containing compound.

Preferred targeting substances useful within the present invention include antibody and antibody fragments including peptide fragments; peptides, such as bombesin, gastrin-releasing peptide, RGD peptide, substance P, neuromedin-B, neuromedin-C, and metenkephalin; and hormones, such as EGF, α- and β-TGF, neurotensin, melanocyte stimulating hormone, follicle stimulating hormone, luteinizing hormone, and human growth hormone. Biotin, avidin, proteins corresponding to known cell surface receptors (including low density lipoproteins, transferrin, insulin and $CD_4$), fibrinolytic enzymes, and biological response modifiers (including interleukin, interferon, erythropoietin and colony-stimulating factor) are also preferred targeting substances. Analogues of the above-listed targeting substances that retain the capacity to bind to a defined target cell population may also be used within the claimed invention. In addition, synthetic targeting substances may be designed by peptide synthetic or recombinant DNA techniques.

By a linker as used herein is generally meant a compound (and its intermediate precursors) which has at least two reactive functional groups on it that will react with at least two compounds to create a complex or adduct between those compounds or which has bonded thereto the two compounds. These compounds can be the same or different, but will in general be different. The reactive functional groups can also be the same or different, but also will generally be different. In particular, a linker of this invention is a rigid bicyclic skeleton having as a first functional reactive group an anhydride moiety which is reactive with, e.g., a free amino group of an amino-group-containing compound, and a linker arm attached to the bicyclic skeleton which contains at its distal end, i.e., away from the bicyclic skeleton, a second reactive functional group.

This second functional group is then covalently linked to a second agent, which is generally a targeting agent, to form the complex of active agent-linker-targeting agent. However, it is noted that, when the acid-cleavable linker of this invention is used to attach a targeting agent to a support material, the amino group attached to the bicyclic skeleton may be derived from either the targeting agent or the support material; when the amino group attached to the bicyclic skeleton is derived from the targeting agent, the reactive group attached to the linker arm is covalently linked to the support material, which replaces the targeting agent in the general description given above.

By "substance having a group which selectively binds to a targeting agent" as used herein is meant a wide variety of materials which may contain any group to which a targeting agent can bind, including haptans, ligands, antigens, proteins including antibodies, as well as larger materials having such binding materials substantially attached, e.g., whole cells or fragments thereof which have groups to which targeting agents can bind attached to, e.g., their cell surfaces.

Suitable support materials are any of the many conventional materials which are known in the art for use as a physical solid phase support, e.g., for separations of components from a liquid phase. They may already contain suitable reactive groups, e.g., amino or sulfhydryl groups, for attachment using the linker of this invention, or they can be routinely modified by one of ordinary skill in the art to contain suitable such reactive groups. Non-limiting examples of such support materials include carboxymethylcellulosic materials, acrylamide-based support materials, derivatized silyl materials, etc.

Without wishing to be bound by theory, it is believed that a key structural requirement for amide hydrolysis catalyzed by an adjacent carboxylic acid group is a rigid geometry which provides a template holding the two reacting functional groups in the correct reaction geometry. See, e.g., Kirby et al. and Aldersley et al., supra, and Kluger, R. and Lam, C.-H., JACS 100, 2191–2197 (1978). Moreover, this hydrolysis reaction is believed to be initiated by protonation of the carboxylic acid group. Thus, the rate of reaction for a given substrate at a particular pH value is determined in part by the $PK_a$ of the carboxylic acid proton. Consequently, varying the structure of the linker of this invention such that the $pK_a$ is varied provides a useful degree of freedom to match the $PK_a$ to contemplated pH conditions at which cleavage is desired. For example, substituents which force the carboxylic acid and the amide groups closer together accelerate the rate of hydrolysis. Conversely, substituents which pull the two reactive groups apart slow the reaction. Preferred such variations are discussed below.

It is theoretically also possible for there to be an effect on hydrolysis rates due to structural variations in the amido side chain. These, however, are relatively minor, whereby the widest variety of amino-containing active agents will be applicable to this invention (Kluger and Lam, supra).

A preferred rigid bicyclic skeleton is [2.2.1] bicycloheptane, commonly referred to as norbornane. Other rigid bicyclic skeletons are also suitable, including, e.g., the [2.2.2]bicyclooctane skeleton.

A bicyclic skeleton is superior for several reasons to the maleamic acid-based linker of U.S. Pat. No. 4,569,789. The carboxylic acid of the present invention is more like an aliphatic (i.e., saturated) acid, even if double bonds are present in the skeleton, so long as they are not adjacent to the carboxyl group. In general, unsaturated carboxylic acids have lower $pK_a$s and are thus stronger acids than aliphatic acids. Therefore, assuming geometric constraints are equivalent, an acid-cleavable linker utilizing an aliphatic carboxylic acid group to catalyze the amide hydrolysis would hydrolyze the amide bond faster than a linker utilizing an unsaturated carboxylic acid at the same pH. It is more likely that the $PK_a$ of an aliphatic carboxylic acid will more closely approximate the pH of lysosomes than will the $pK_a$ of an unsaturated carboxylic acid.

The bicyclic compounds of this invention can be prepared using conventional chemistry, e.g., Diels-Alder reactions. For example, the construction of the [2.2.1], [2.2.2] and [2.2.3] bicyclic skeletons is shown below. Variations of the ring size n, introduction of substituents onto the bicyclic skeleton and manipulation of a double bond, e.g., the 5,6-double bond in a norbornene produced by the Diels-Alder chemistry, by oxidation/reduction provide a variety of approaches to "fine tune" the hydrolysis kinetics by introducing or relieving ring strain, or providing steric or electronic effects in the rigid framework of the bicyclic skeleton.

Suitable substituents on the bicyclic skeleton, e.g., for affecting the rate of reaction of hydrolysis of the amide group, the $pK_a$, or solubility, etc., include a wide variety of substituents, which will have a variety of predictable or easily determinable effects upon these characteristics. For example, suitable substituents which will have a tendency to increase the rate of the hydrolysis reaction, particularly when positioned on the carbon atom from which the carboxyl group depends, include electron donating groups, e.g., hydrocarbons. Conversely, substituents which will have a tendency to decrease the rate of the hydrolysis reaction, particularly when similarly situated, include electron withdrawing groups, e.g., oxygen, nitrogen, carbonyl-, nitro-, cyano- or halogen-containing groups. Furthermore, in general, bulky groups substituted at the 2- and 3-position will tend to force the reactive carboxyl and amido groups closer together, thus increasing the rate of hydrolysis.

Preparation of the bicyclic skeleton for the linker can be approached in various ways. In general, construction of the bicyclic skeleton is easily accomplished using Diels-Alder chemistry. The Diels-Alder reaction is one of the most well-understood and generally applicable reactions in organic chemistry. See, e.g., Kloetzel, M. C., Org. Reac. 4, 1–59 (1948); Holmes, H. L., Org. Reac. 4, 60–174 (1948) and March, J., *Advanced Organic Chemistry, 3rd ed., John Wiley and Sons, New York, pp.* 745–758 (1985). Although attachment of a linker arm is possible by functionalizing the double bond of the Diels-Alder adduct or the upper liner bridge, a more straightforward approach involves the incorporation of the linker into the maleic anhydride moiety prior to the Diels-Alder reaction. Another advantage of this approach is that the double bond can remain available to either "fine tune" the hydrolysis kinetics or to add functional groups, e.g., polar groups such as vicinal dihydroxy groups to improve the solubility of the linker. Construction of the linker by two of these approaches is summarized in FIGS. 1 and 3. If the double bond is not desired, it can be reduced by means well known to one of ordinary skill in the art, e.g., using a Paar hydrogenation apparatus.

The precise nature of the linker arm is not critical in accordance with this invention. Essentially any bridging group can be utilized which is derived from a precursor of the bridging group, i.e., a compound which is used to form the linker arm in the preparation of the conjugates of this invention, which provides means for effecting attachment to the bicyclic skeleton and means for attachment to the targeting agent. Very often, amino acid or peptide linker arms will be utilizable. In general, linker arms in the range of 1–12 carbon atoms in length are preferred, as larger groups may cause solubility problems. Of course, these solubility problems can also be obviated, if longer linker arms are desired, by routine modification of, e.g., the linker arm, with groups which enhance solubility, e.g., polar groups, e.g., hydroxyl groups. In addition, the linker arms can themselves be substituted, e.g., by the addition of OH groups, to increase the solubility of the resulting complex.

The distal end of the linker arm can be constructed such that the linker is heterobifunctional, although homobifunctional uses and linkers can also be envisaged. Since the anhydride portion of the linker on the bicyclic skeleton is designed to react with an amine on the active agent, the reactive group at the other end of the linker arm should be capable of reacting with a different moiety on the targeting agent from the amino moiety of the active agent which is to be covalently bonded to the anhydride portion of the linker, e.g., the second reactive group could be reactive with a sulfhydryl moiety on an antibody. In addition, this linker arm can be selected or modified by means well known in the art to provide beneficial properties, i.e., solubility properties, to the linker.

Thus, in summary, the exact nature of a suitable linker arm is not important so long as it has appropriate characteristics. For example, it should be easily attached to the bicyclic skeleton under reaction conditions which do not affect either the anhydride portion of the adduct or the active agent; it should be long enough to allow the group which is to be attached to it to be sterically unhindered, both in the coupling reaction and in any subsequent binding reaction necessary for its targeting function; it should be short enough to ensure that the active agent will be localized at essentially the same locus as the second portion of the adduct, and so that it does not interfere with the solubility of the overall complex; and it should contain a reactive group on it which is capable of reacting with the second portion of the adduct, and, preferably, is not capable of reacting with the active agent, or which can be selectively blocked and then unblocked to ensure that the active agent portion is only linked through the cleavable amide linkage to the linker.

Introduction of the linker arms onto the bicyclic skeleton is accomplished either by introducing the substituents onto the cycloanhydride and/or cyclodiene prior to the Diels-Alder reaction, or by substituting the bicyclic skeleton once formed by the Diels-Alder reaction. In general, substitution of the monocycles is preferred, particularly of the anhydride portion; however, introduction of the linker arm is also relatively simply performed by reduction and substitution of a double bond present in the bicyclic skeleton; for example, the 5,6-double bond present in the norbornene adduct.

One simple candidate for a suitable linker arm is a functionalized cysteine group. Two heterobifunctional linkers utilizing this linker can thus be synthesized according to the reaction schema shown in FIGS. 1 and 2.

Suitable groups for forming the distal, reactive end of the linker arm for covalent attachment of proteins include those disclosed in, e.g., Means, G. E. and Feeney, R. F., *Chemical Modification of Proteins*, Holden-Day, San Francisco (1974). Generally, for the case when the targeting agent to be attached is an antibody, or other sulfhydryl-containing protein, groups such as N-substituted maleimides are known to be especially suitable. In general groups such as, e.g., Michael-type acceptors, e.g., maleimides, and activated halides, e.g., iodoacetamides and bromoacetamides, can be employed as the reactive group. In addition, other reactive groups can be employed at the distal end of the linker to provide a means for attachment based upon other types of chemistry; for example, groups can be used for linking an amino group of, e.g., a protein targeting agent, to the linker arm, for example, activated esters, e.g., N-hydroxysuccinimidyl esters, sulfosuccinimidyl esters, thiophenyl esters, 2,3,5,6-tetrafluorophenyl esters, and 2,3,5,6-tetrafluorothiophenyl esters. Of course, in the case where an amino-reactive group is used as the targeting agent conjugation reactive group, the acid-cleavable group will have to be reacted first, in order to avoid spurious linkages from being formed.

The linker is generally first prepared in the form of a linker precursor, comprising the bicyclic skeleton with a linker arm and reactive group on the linker arm attached. Depending upon the chemistry of the reactions involved, e.g., the pH at which the linker precursor is prepared, the carboxyl groups at the 2- and 3-positions of the bicyclic skeleton may be either in the form of the free carboxyls, may be modified or blocked by a protecting group, or they may be in the form of an anhydride. Unless already in anhydride form, the linker precursor is then conventionally treated to prepare the anhydride form prior to reaction with the amide group of the active agent.

Thus, in a preferred embodiment, the active agent containing an amino group is first reacted with the linker precursor, which has been constructed to contain a linker arm and a second reactive group which is reactive with a sulfhydryl group, by amidating the anhydride of the linker precursor. Suitable conditions for reacting amines with anhydrides are well known to one of ordinary skill in the art, and optimal conditions for any particular set of reactants are routinely determinable. Next, the targeting agent, which is preferably a protein, and most preferably an antibody which contains sulfhydryl groups, is covalently linked to the active agent/linker conjugate through the precursor of the reactive group that is reactive with sulfhydryl groups. Other known heterologous reactive groups (i.e., non-amino reactive) are also fully equivalent according to this invention with sulfhydryl reactive groups.

However, as noted above, also encompassed by this invention are linkers in which reactive groups which are reactive with the same moiety on both the active agent and the targeting agent, e.g., an amino group, are produced by sequential additions. Thus, the linker is synthesized to contain an anhydride portion, the active agent is added to the anhydride to form the acid-cleavable bond, then the linker arm containing another amino-reactive group is added, e.g., through reduction of the 5,6-double bond of the bicyclic skeleton (or the equivalent in skeletons containing a different number of carbon atoms), and an amino-containing targeting agent is linked thereto.

In designing suitable linker compounds, the geometry of the bicyclic skeleton must also be taken into account. For example, in this invention the carboxyl and amide groups of the linker are on the same side of the plane of the skeleton, i.e., syn-, in order to facilitate the subsequent acid hydrolysis reaction. Furthermore, the bicyclic skeleton must maintain a suitable geometry which facilitates the hydrolysis reaction. For example, the skeleton from which the carboxyl and amino groups depend preferably contains at least six carbon atoms or the equivalent (e.g., N, O or S atoms) in order to provide the appropriate geometry for the reaction, in that the carboxyl and amide groups are close enough together to interact with a useful $T_{1/2}$.

Bicyclic compounds of the type disclosed above have the required rigidity of structure and geometry for maintaining the appropriate relationship between the carboxyl and amide moieties which will facilitate hydrolysis of the amide at the appropriate pH. However, it is also possible that other, e.g., polycyclic, structures will provide the same or similar functional aspects of this invention while not adhering precisely to the noted structure, yet are considered to be fully equivalent to this invention. For example, rigid skeletons having a third or additional ring structure, either saturated, unsaturated or aryl, can be envisioned, particularly depending from the 5,6-position, and which have essentially the same acid-cleavable characteristics as the bicyclic acid-cleavable linker of this invention are fully encompassed by the meaning of substituted bicyclic skeleton.

The chemistry described above can be performed in essentially any order. For example, the various portions of the molecule can be prepared in any order as may be most convenient for a given application. Similarly, all or part of the chemistry can be performed before or after chelation of a given metal. It is generally preferred to attach the targeting agent as the last step to avoid interfering reactions with its functional group.

Thus, in accordance with this invention, any desired diagnostic or therapeutic agent can be cleavably linked with an appropriate targeting group to optimize the desired effect on a locus in a patient, e.g., by appropriately matching an agent effective at a locus with a moiety able to target that locus.

Intracellular release of a cytotoxic agent, a chelating ligand plus agent or a radionuclide from a targeting substance conjugate may be desirable in many instances. In this regard, the claimed diagnostic or therapeutic targeting substance conjugates provide serum stability during delivery of the conjugate to an appropriate target cell. Upon internalization of the conjugate into target cell endosomes, the attached cytotoxic agent or radionuclide is released in the low pH environment, which in turn may facilitate translocation of the diagnostic or therapeutic agent or radionuclide from the target cell endosome into the cytoplasm. In the case of certain proteinaceous agents, translocation into the cytoplasm would allow the agent to escape degradation in target cell lysosomes.

Some proportion of administered targeting substance conjugate may bind to normal cells of the mammalian recipient. Typically, if antibody is conjugated to a radiometal using non-cleavable bifunctional linkers, accumulation of significant amounts of radionuclide in normal tissues (i.e., liver and bone marrow) by receptor-mediated endocytosis is observed.

In contrast, the conjugate of this invention provides a reversible (acid-cleavable) attachment of the diagnostic/therapeutic agent to a targeting substance. The claimed conjugate will provide reduced accumulation of the radionuclide in normal tissues, through release of the covalently attached radiometal into the acidic environment of the normal cell endosome/lysosome. As a result, the diagnostic/therapeutic agent (with or without chelator) may be subject to accelerated metabolism and excretion by the normal cell. When the agent is shunted out of the normal cell, it is returned to the bloodstream and rapidly excreted by the kidney, rather than accumulating in normal tissues.

This invention will also be applicable to target-specific delivery of a diagnostic moiety which need not be cleaved in situ, as well as to therapeutic agents which are able to exert their therapeutic effective without being cleaved.

The conjugates of this invention will typically be administered for the same purposes as the amino-containing therapeutic or diagnostic agent is administrable. Thus, daunomycin targeted in accordance with this invention will be administrable for anti-tumor treatment analogously to the methods heretofore used to employ this chemotherapeutic agent in the treatment of cancer. Generally, suitable dosages will be in the same ranges conventionally known for the therapeutic or diagnostic agent. In many instances, the dosage of the therapeutic or diagnostic agent necessary may be reduced in view of the increased selectivity effected by this invention. Suitable dosages will vary according to such factors as the nature of the patient's illness, the number and location of target sites, any cross-reactivity of the targeting moiety with normal tissues, etc. A physician skilled in the field to which this invention pertains will be able to determine routinely the proper dosage of a particular conjugate of the present invention.

For example, for radionuclide chelates, administration will be, as is conventional, by injection, intravenously, intra-arterially, peritoneally, intratumorally, etc., depending on the particular site desired. Without limiting this invention, typically, from 0.001 to 50 mCi/kg of host will be used. For human hosts, the dosage will usually be about 10–50 mCi/70 kg of host, more usually about 25–35 mCi/70 kg of host. For lower mammals, e.g., mice, 1 mCi for biodistribution studies will be employed, while up to or greater than 500 mCi for imaging studies can be used. After administration of the diagnostic agent, e.g., radionuclide or paramagnetic metal, the host will be treated conventionally for detection or imaging. Where treatment is involved, similarly, subsequent procedure will be as is conventional.

The compounds of this invention can be administered in the usual galenic formulations and can be provided in the form of the usual kits. For example, a kit could comprise a container of the linker, including a suitable targeting-agent conjugation group, attached to a therapeutic or diagnostic agent, as described above, and a container of the targeting agent to be attached thereto. Alternatively, a kit could comprise a container of the linker, including a suitable targeting-agent conjugation group, which is in a form that is, or can be converted to a form that is, reactive with a therapeutic or diagnostic agent, and additional vials of one or more of the therapeutic or diagnostic agent and/or the targeting agent. In some cases, it will be most suitable for the targeting agent to be specially prepared for the particular patient, in which case the targeting agent will be added by the methods described at or near the time of treatment.

Suitable pharmaceutically acceptable adjuvants will be all inorganic and organic compounds known for this purpose, e.g., including water, saline, buffers, antioxidizing agents (e.g., ascorbic acid), surfactants (e.g., lecithins, Tween®, Myrj®), etc., as long as these adjuvants do not have an adverse impact on the targeting agent or the therapeutic or diagnostic agent, and do not facilitate premature cleavage of the amide bond.

The acid-cleavable linker of this invention can also be used in an in vitro variation of the targeting method of this invention, by using it to bind a targeting agent to a support material for separations based upon the ability of the targeting agent to bind selectively to particular groups on a substance, and subsequent release of the bound substance by acid hydrolysis under milder conditions than are usually available for reversal of such binding. For example, it would be very useful to be able to select a particular cell type out of a mixture of cell types, e.g., to isolate T-cells from a heterogeneous population of blood cells, based upon the ability of a cell-surface component specific to the desired cell type to bind to a targeting group specific for said component. In fact, such binding is possible using current technology, allowing the binding of particular desired cell types to a targeting agent bound to a support material, but the problem of subsequent release of the bound cells remains a problem. Various methods of release, e.g., treatment with urea, high salt, mechanical agitation, etc., have been used, but each has its obvious drawbacks, including, most particularly, damage to the material which is to be isolated.

In contrast, by use of the acid-cleavable linker of this invention, it is possible to link a targeting agent to a support material by a bond which is easily cleaved under mild acid conditions which are not harmful to such biological material. This linkage is flexible, in that it can be obtained by linking the targeting agent to the support material by a linker in either orientation, i.e., by an amido group from either the support material or from the targeting agent, with the other end of the linkage in each case being through a reactive group on the linker arm attached to the bicyclic skeleton as discussed above. Of course, in the case where the acid cleavable linkage is to an amino group directly attached to the support material, the resultant product after acid cleavage is the substance having the group which selectively binds to a targeting agent, the targeting agent bound thereto, and the bicyclic portion of the linker. In the case where the acid cleavable linkage is to an amino group attached to the targeting agent, the resultant product after acid cleavage is just the substance having the group which selectively binds to a targeting agent and the targeting agent bound thereto. The targeting agent (and bicyclic portion of the linker, if still attached) may then be removed by other conventional means, if necessary, or, in many cases is not removed, especially when the presence of such a group bound to the substance, e.g., to the cell, is not incompatible with or detrimental to its subsequent use.

Support materials having targeting agents linked thereto are made by methods analogous to those described above for linking active agents to targeting agents. Thus, in the case where the support material bears the amino group, the bicyclic linker is made as described above, with or without the targeting agent already attached, depending routinely upon the chemistry being used to attach the targeting agent, the linker is then attached to the support material via the amino group, and, if necessary, the targeting agent is then attached. Similarly, when the linker is attached to the targeting agent through the acid cleavable bond, the bicyclic portion of the linker is made as described previously, and then, again, depending upon the chemistry, is attached to the targeting agent first and then to the support material, or vice versa.

Support materials having targeting agents acid-cleavably linked thereto are used by methods anagolous to the well-known methods of using other support materials. The methods of preparing the support material, including packing columns containing such materials, if desired, are well known. Methods of and suitable conditions for binding the appropriate substances to the column andwashing off the unbound substances are similarly well known. After such routine methods have been performed, it is a simple matter of subjecting the support material linked to the targeting agent through the acid-cleavable bond and the desired substance bound to the targeting agent to mild acid conditions sufficient to hydrolyze the acid-cleavable linker and thereby release the desired substance and bound targeting agent (and bicyclic portion of the linker, if still attached). Such mild acid conditions are routinely determinable by one of skill in the art, and are preferably those which cleave the linker at a physiologically compatible pH in a physiologically reasonable amount of time, as noted above, and which conditions are not detrimental to the substance being isolated.

Thus, this invention also provides a bicyclic non-aromatic hydrocarbon compound, optionally having one or more N, O or S atoms in the bicyclic skeleton, and having as substituents an acid group and an amido group which are vicinal and in a syn-position, wherein

- the acid group is carboxyl or carboxyl in a form metabolizable to a free carboxyl group,
- said bicyclic skeleton is optionally unsaturated except in the bond between said groups,
- the amido group is acid-cleavable,
- the bicyclic ring is further substituted by a linker arm having a reactive group which is covalently linked to a targeting agent or to a support material, and
- the amido group is derived from a targeting agent when the reactive group on the linker arm is covalently linked to a support material, and is derived from a support material when the reactive group on the linker arm is covalently linked to a targeting agent.

This invention further provides a support material having a targeting agent linked thereto by an acid-cleavable linker comprising

- a support material having an attachment group attached thereto which group is covalently linked to an acid-cleavable linker, wherein said linker comprises
  - a bicyclic non-aromatic hydrocarbon compound, optionally having one or more N, O or S atoms in the bicyclic skeleton, and having as substituents an acid group and an amido group which are vicinal and in a syn-position, wherein the acid group is carboxyl or carboxyl in a form metabolizable to a free carboxyl group, said bicyclic skeleton is optionally unsaturated except in the bond between said acid and amido groups, the amido group is acid-cleavable, the bicyclic ring is further substituted by a linker arm having a reactive group which is covalently linked to the targeting agent or to the attachment group of the support material, and the amido group is derived from the targeting agent when the reactive group on the linker arm is covalently linked to the attachment group of the support material, and is derived from the attachment group of the support material when the reactive group on the linker arm is covalently linked to the targeting agent.

Still further, this invention provides a method of isolating a substance having a group which selectively binds to a targeting agent, comprising contacting a mixture containing said substance with the support material described above under conditions wherein the targeting agent will bind to the group on said substance for which it is selective, washing unbound components of the mixture off of the support material, sujecting the support material to acid conditions sufficient to cleave the acid-cleavable linker, and isolating the substance from the support material, and, in particular, to a method of isolating cells of a desired cell type from a mixture of cells.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications cited above and below are hereby incorporated by reference.

EXAMPLES

Example 1

Synthesis of linker 6

To a solution of 2-(bromomethyl)maleic acid (5.0 g, 24 mmol) in water (50 mL), and 1N NaOH (35 mL) which has been degassed with $N_2$, is added a solution of N-(tert-butoxycarbonyl) cysteine methyl ester (5.6 g, 24 mmol) in degassed ethanol (EtOH) (50 ml). The resulting solution is stirred at room temperature under $N_2$ for 1 hour. The solution is then chilled by the addition of ice and acidified with 1N HCl (40 mL). The solvents are evaporated under reduced pressure to approximately one half the original volume. The product is extracted with ethyl acetate (EtOAc), washed with saturated NaCl and dried over $Na_2SO_4$. The solution is filtered and the solvents are evaporated under reduced pressure to afford 1.

To a solution of 1 (5.0 g, 14 mmol) in anhydrous THF (75 mL) is added a solution of 1,3-dicyclohexylcarbodiimide (3.2 g, 15.5 mmol) in THF (35 mL). After 12 hr at room temperature the solution is filtered to remove the precipitated dicyclohexylurea and concentrated to dryness under reduced pressure. The sample is resuspended in THF, filtered, and the solution is then concentrated to dryness under reduced pressure to afford 2. Compound 2 is further purified by flash chromatography.

To a solution of 2 (3.0 g, 8.7 mmol) in dry benzene (75 mL) under $N_2$ is added freshly prepared cyclopentadiene (0.65 g, 9.8 mmol). The resulting solution is warmed to 50° C. for several hours. The benzene is then removed by evaporation at reduced pressure to afford 3.

To a solution of 3 (1.0 g, 2.4 mmol) in THF (20 mL) is added 1N NaOH (5.0 mL, 5.0 mmol). The resulting solution is stirred at room temperature for several minutes then acidified with 1N HCl (5.0 mL, 5.0 mmol) and extracted with EtOAc. The extracts are dried over $Na_2SO_4$, filtered, and the solvents evaporated to dryness under reduced pressure. The product is suspended in ether/EtOH (15 mL, 1:1 v/v) and treated with a solution of p-toluenesulfonic acid monohydrate (0.46 g, 2.4 mmol) in EtOH (5.0 mL). After several hours a couple drops of water are added and the solvents are evaporated under reduced pressure to afford 4.

A solution of 4 (1.0 g 2.0 mmol) is prepared in anhydrous THF (15 mL) and chilled in an ice bath. To this solution is added N-ethylmorpholine (1.3 mL, 10.2 mmol) followed by the dropwise addition of a solution of 6-maleimidocaproyl chloride (0.69 g, 3.0 mmol) in anhydrous THF (3.0 mL). After several hours the solution is evaporated to dryness under reduced pressure. The product is suspended in EtOAc, washed with dilute HCl, saturated NaCl, and dried over $Na_2SO_4$. The solution is filtered and evaporated under reduced pressure to afford 5.

A solution of 5 (0.26 g, 0.50 mmol) in anhydrous THF (4.0 mL) is treated with a solution of 1,3-dicyclohexylcarbodiimide (0.13 g, 0.63 mmol) in THF (1.0 mL). After 12 hr at room temperature, the solution is filtered to remove the precipitated dicyclohexylurea and concentrated to dryness under reduced pressure. The sample is resuspended in THF, filtered, and the solution is then concentrated to dryness under reduce pressure to afford 6. Compound 6 is further purified by flash chromatography.

This reaction scheme is summarized in FIG. 1.

Example 2

Syntheses of linker 8.

A solution of 4 (4 synthesized in Example 1) is prepared in saturated $NaHCO_3$ (15 mL) and chilled in an ice bath. To the above solution is added N-methoxycarbonyl-maleimide (0.39 g, 2.5 mmol). After several minutes the solution is diluted with THF (20 mL) and stirred at 40° C. for an hour. The solution is then brought to pH 6–7 by the addition of $H2SO_4$, evaporated to approximately one-half volume under reduced pressure. The solution is further acidified to pH 1–2 by the addition of $H_2SO_4$ and extracted with EtOAc. The extracts are washed with saturated NaCl and dried over $Na_2SO_4$. The solution is filtered and evaporated to dryness under reduced pressure to afford 7. Compound 7 is further purified by flash chromatography.

A solution of 7 (0.20 g, 0.50 mmol) in anhydrous THF (4.0 mL) is treated with a solution of 1,3-dicyclohexylcarbodiimide (0.13 g, 0.63 mmol) in anhydrous THF (1.0 mL). After 12 hr at room temperature the solution is filtered to remove the precipitated dicyclohexylurea and concentrated to dryness under reduced pressure. The sample is resuspended in THF, filtered, and the solution is then concentrated to dryness under reduced pressure to afford 8. Compound 8 is further purified by flash chromatography.

Figure 2:
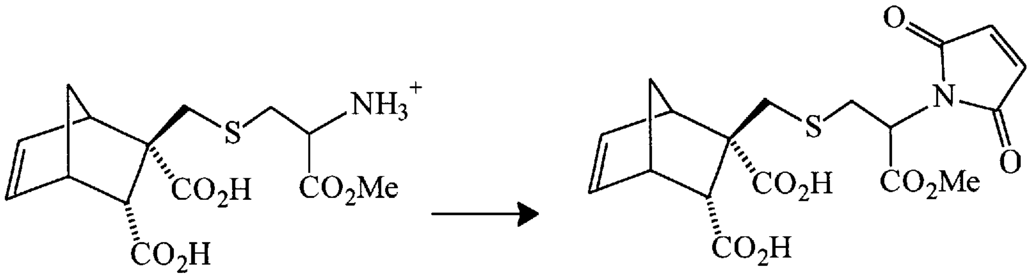
FIG. 2 outlines the reaction pathway described in Example 2.
Figure 2:
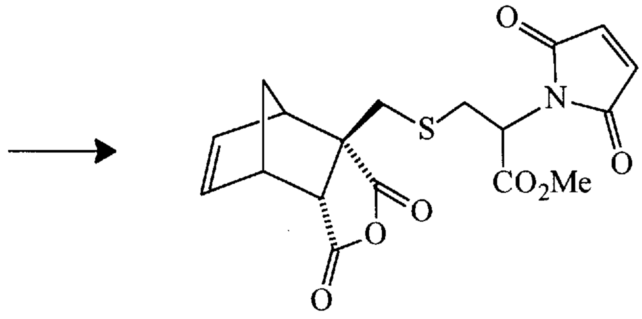

This reaction scheme is summarized in FIG. 2.

Example 3

Syntheses of linker 14.

To a solution of 9 (0.75 g, 2.65 mmol) in THF (20 mL) is added 1N NaOH (5.5 mL, 5.5 mmol). The resulting solution is stirred at room temperature for several minutes then acidified with 1N HCl (5.5 mL, 5.5 mmol) and extracted with EtOAc. The extracts are dried over $Na_2SO_4$ filtered, and the solvents evaporated to dryness under reduced pressure. The residue is dissolved in EtOH (25 mL) and 5% Pd/C (10 mg) is added. The resulting suspension is attached to a Paar hydrogenation apparatus and subjected to $H_2$ gas at 60 psi for several hours. The catalyst is then removed by filtration, and the solvent is evaporated under reduced pressure to afford 10.

To a solution of 10 (0.50 g, 2.3 mmol) in anhydrous $CH_2Cl_2$ (10 mL) and N,N-diisopropylethyl amine (0.90 mL, 5.2 mmol) immersed in an ice bath is added a solution of methanesulfonyl chloride (0.40 mL, 5.2 mmol) in anhydrous $CH_2Cl_2$ (2.0 mL). The resulting solution is stirred at ice bath temperature for several hours then quenched by the addition of water (1.0 mL). The solution is washed with water, dilute HCl, saturated NaCl, and dried over $Na_2SO_4$. The solution is filtered and the solvent is evaporated under reduced pressure to afford 11.

To a solution of 11 (0.5 g, 1.8 mmol) in EtOH (7.5 mL) is added a solution of N-(tert-butoxycarbonyl)-cysteine methyl ester (0.52 g, 2.2 mmol) in EtOH (7.5 ml) followed by 2N NaOH (3.0 mL, 6.0 mmol). The solution is stirred at room temperature for several hours. The solution is chilled by the addition of ice and acidified with 1N HCl (6.0 mL, 6.0 mmol). The EtOH is evaporated under reduced pressure to approximately one-half the original volume. The product is extracted with EtOAc, washed with saturated NaCl, and dried over $Na_2SO_4$. The solution is filtered and the solvents are evaporated under reduced pressure to afford 12.

Compound 12 (0.25 g, 0.61 mmol) is suspended in ether/EtOH (4.0 mL, 1:1 v/v) and treated with a solution of p-toluenesulfonic acid monohydrate (0.12 g, 0.62 mmol) in EtOH (1.0 mL). After several hours the solvents are evaporated under reduced pressure to afford 13.

A solution of 13 (0.25 g, 0.50 mmol) is prepared inanhydrous THF (5.0 mL) and chilled in an ice bath. Tothis solution is added N,N-diisopropylethylamine (0.29 mL, 1.65 mmol) followed by the dropwise addition of a solution of 6-maleimidocaproyl chloride (0.14 g, 0.63 mmol) in anhydrous THF (1.0 mL). After several hours at ice bath temperature the solution is evaporated to dryness under reduce pressure. The product is extracted with EtOAc, washed with dilute HCl and dried over $Na_2SO_4$. The solution is filtered and the solvent evaporated to dryness under reduced pressure. The material is dissolved in anhydrous THF (4.0 mL) and treated with a solution of 1,3-dicyclohexylcarbodiimide (0.13 g, 0.63 mmol) in anhydrous THF (1.0 mL). After 12 hr at room temperature the solution is filtered to remove the precipitated dicyclohexylurea and concentrated to dryness under reduced pressure. The sample is resuspended in THF, filtered, and the solution is then concentrated to dryness under reduced pressure to afford 14. Compound 14 is further purified by flash chromatography.

Figure 3:
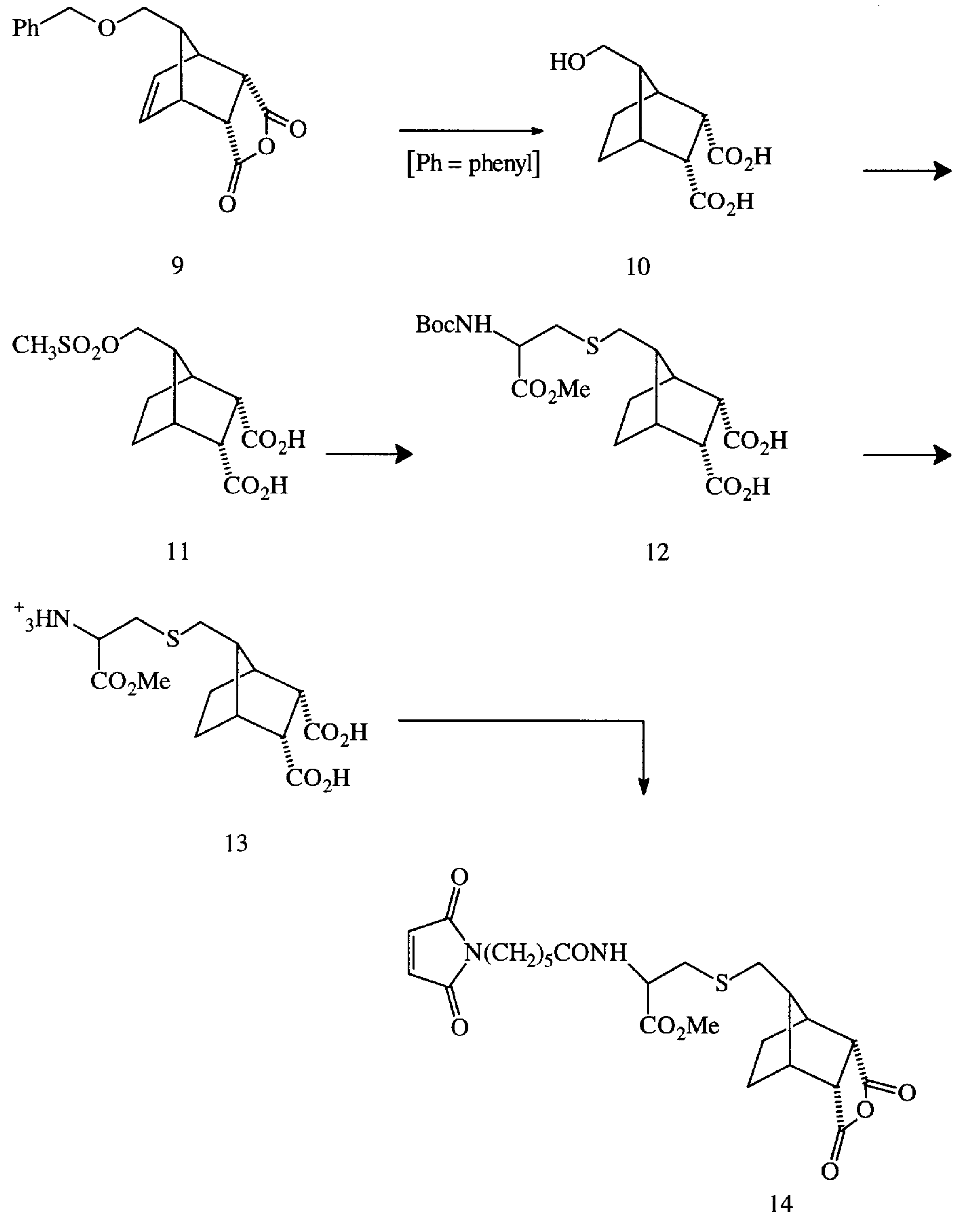
FIG. 3 outlines the reaction pathway described in Example 3.

This reaction scheme is summarized in FIG. 3.

Example 4

Reaction of a Drug (Daunomycin) with Linker 14.

To a solution of Daunomycin (5.0 mg, 9.5 mmol) in 0.1M $Na_2PO_4$ (1.0 mL) in an ice bath is added a solution of 14 (6.0 mg, 11.8 mmol) in tetrahydrofuran (0.5 mL). The pH is kept at 9 by the addition of 1.0N NaOH. The solution is used directly in Example 6 below.

Figure 4:
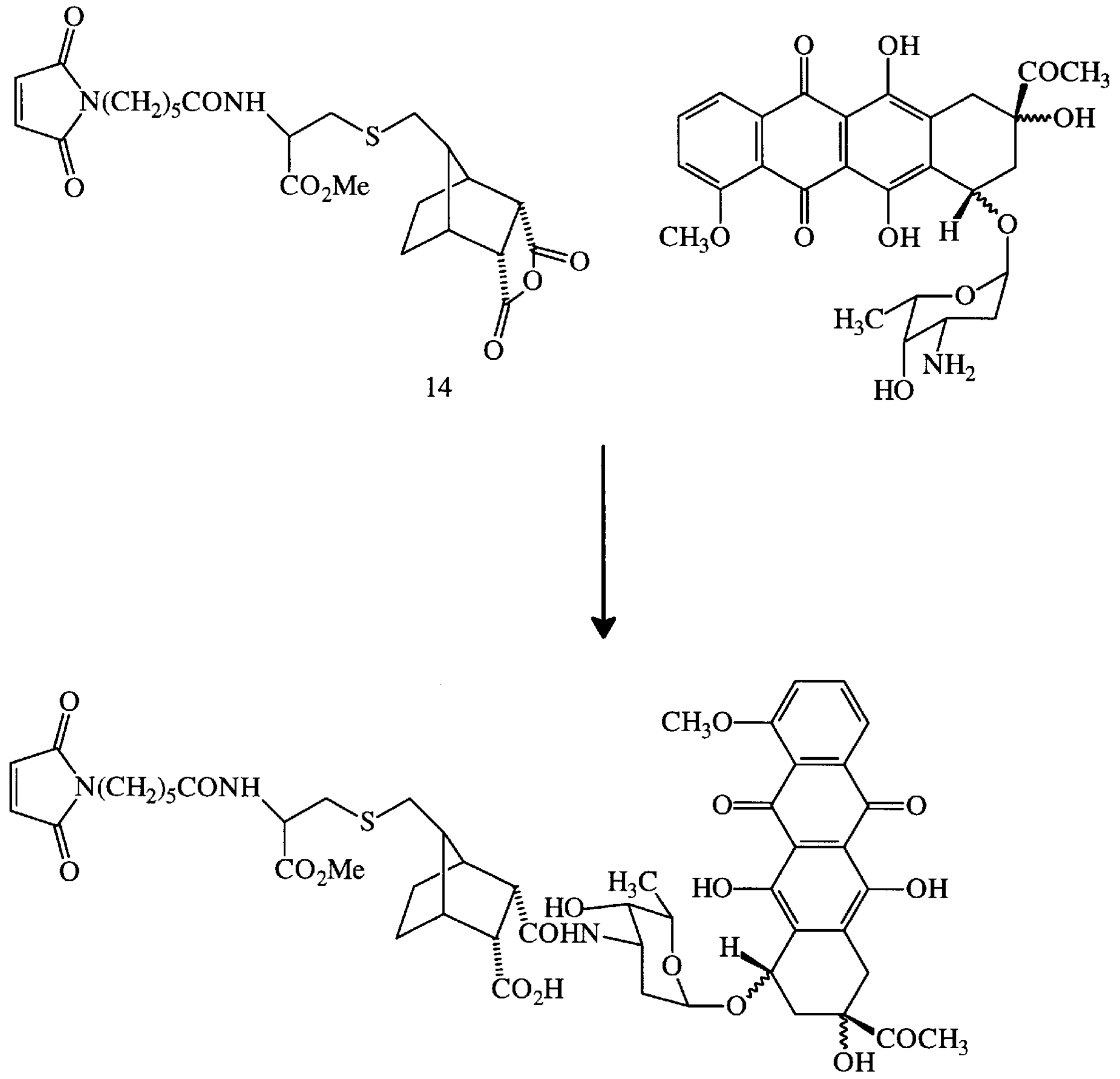
FIG. 4 outlines the reaction pathway described in Example 4.

This reaction scheme is summarized in FIG. 4.

Example 5

Reaction of a Toxin (Pseudomonas exotoxin) with linker 14.

To a solution of Pseudomonas exotoxin (PE; 5 mg/mL in phosphate-buffered saline [PBS], pH 8.5) is added a solution of 14 in an appropriate polar solvent (i.e. tetrahydrofuran, ethanol, dimethylformamide, dimethylsulfoxide etc.) in an amount to achieve to the desire level of derivatization of PE. The reaction is agitated at room temperature for 30 minutes, and purified by passing the reaction mixture through a PD-10 column (Pharmacia, Uppsala, Sweden) eluting with PBS, pH 7.5.

Figure 5:
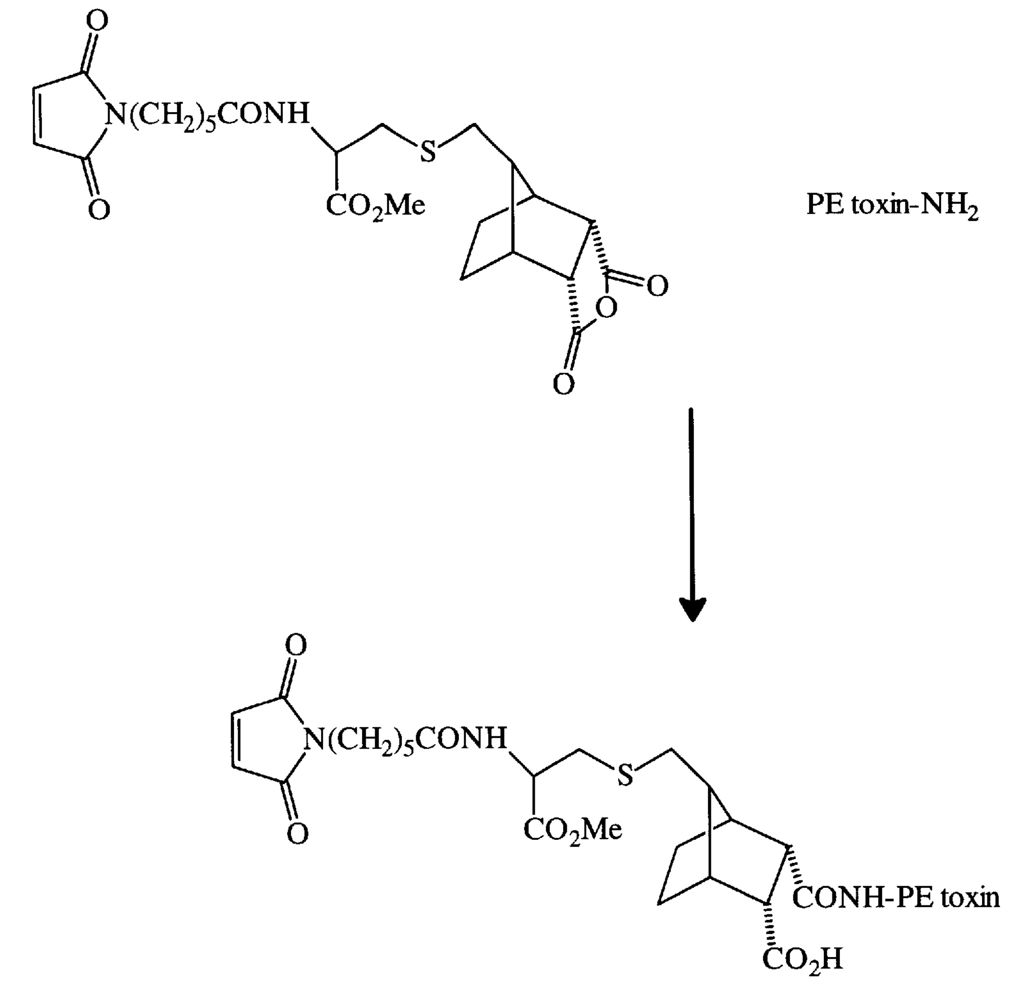
FIG. 5 outlines the reaction pathway described in Example 5.

This reaction scheme is summarized in FIG. 5.

Example 6

Formation of Targeting Substance Drug Conjugate using Targeting Substance Sulfhydryls.

Formation of a targeting protein conjugate is accomplished by treating a monoclonal antibody (MAb; 5 mg/mL in PBS, pH 8.5) with 10 mM dithiothreitol (DTT). The reaction mixture is agitated at room temperature for 30 minutes, and the reduced MAb is passed through a PD-10 column eluting with PBS, pH 6.5 to remove unreacted DTT.

The reduced MAb solution (1.0 mg/mL in PBS, pH 6.5) is treated with a solution of the drug derivatized with the linker (as per Example 4) at the desired concentration to achieve the desired level of derivatization of the MAb. The MAb-linker-drug conjugate is purified by passing the reaction mixture through a PD-10 column.

Figure 6:
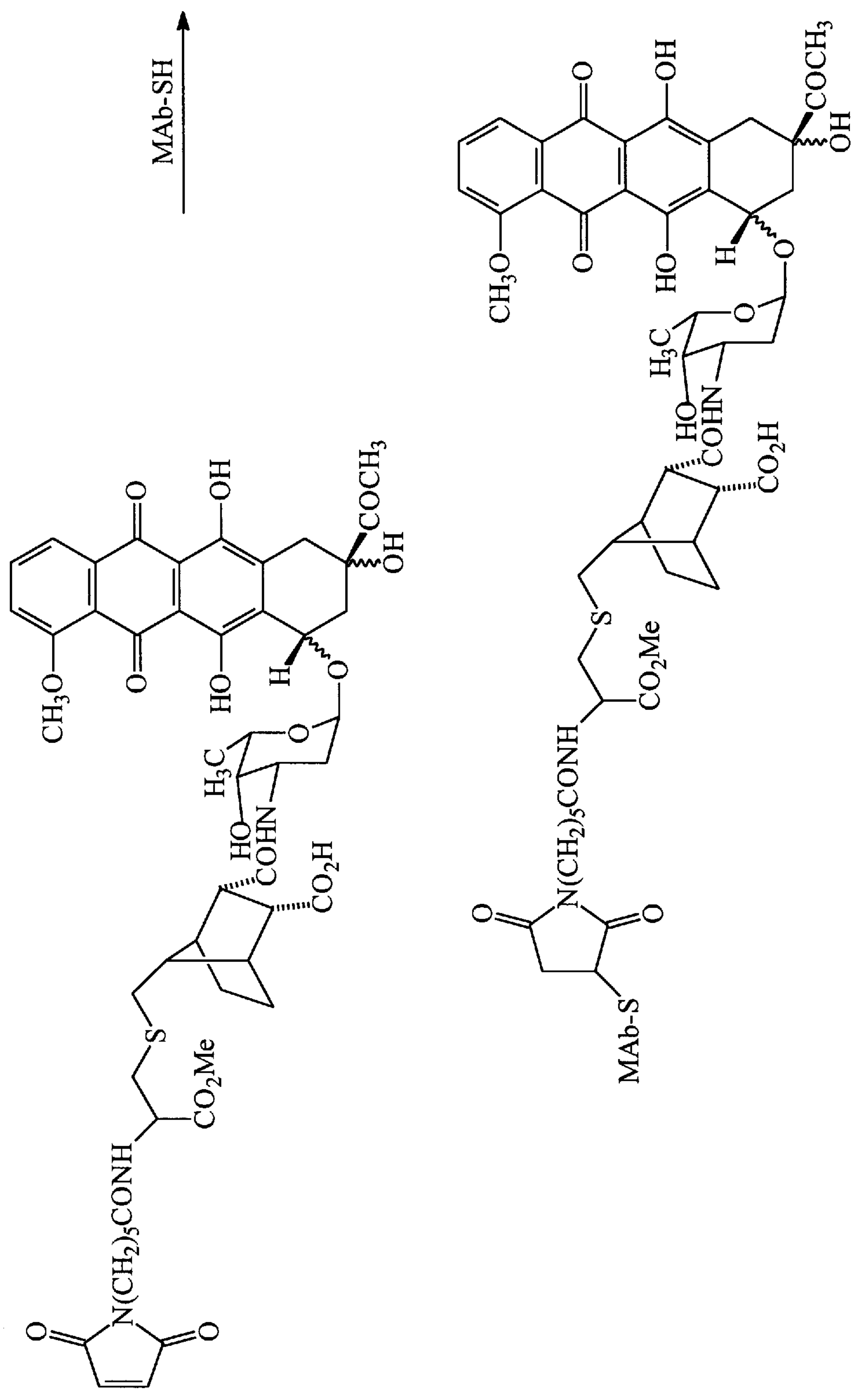
FIG. 6 outlines the reaction pathway described in Example 6.

This reaction scheme is summarized in FIG. 6.

Example 7

Formation of Targeting Substance Drug Conjugate using Targeting Substance Lysines.

Monoclonal antibody (MAb; 5 mg/mL in PBS, pH 7.0) in 0.4M sodium borate, pH 8.0 is treated with iminothiolane (IT); the amount of IT offered to the MAb preparation will be dependent upon the number of free MAb sulfhydryls desired. The reaction of IT with targeting substance lysines is schematically represented as follows:

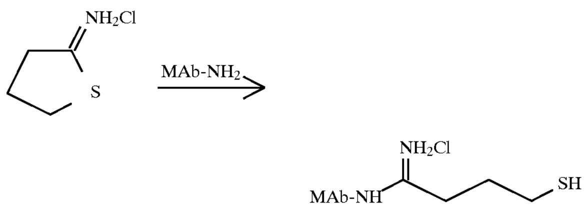

The reaction mixture is agitated at room temperature for 30 minutes, and the reduce MAb is passed through a PD-10 column eluting with PBS, pH 6.5 to remove unreacted IT.

The sulfhydryl-derivatized MAb solution (1.0 mg/mL in PBS, pH 6.5) is treated with a solution of the drug derivatized with the linker (as per Example 4) at the desired concentration to achieve the desired level of derivatization of the MAb. The MAb-IT-linker-drug conjugate is purified by passing the reaction mixture through a PD-10 column.

Figure 7:
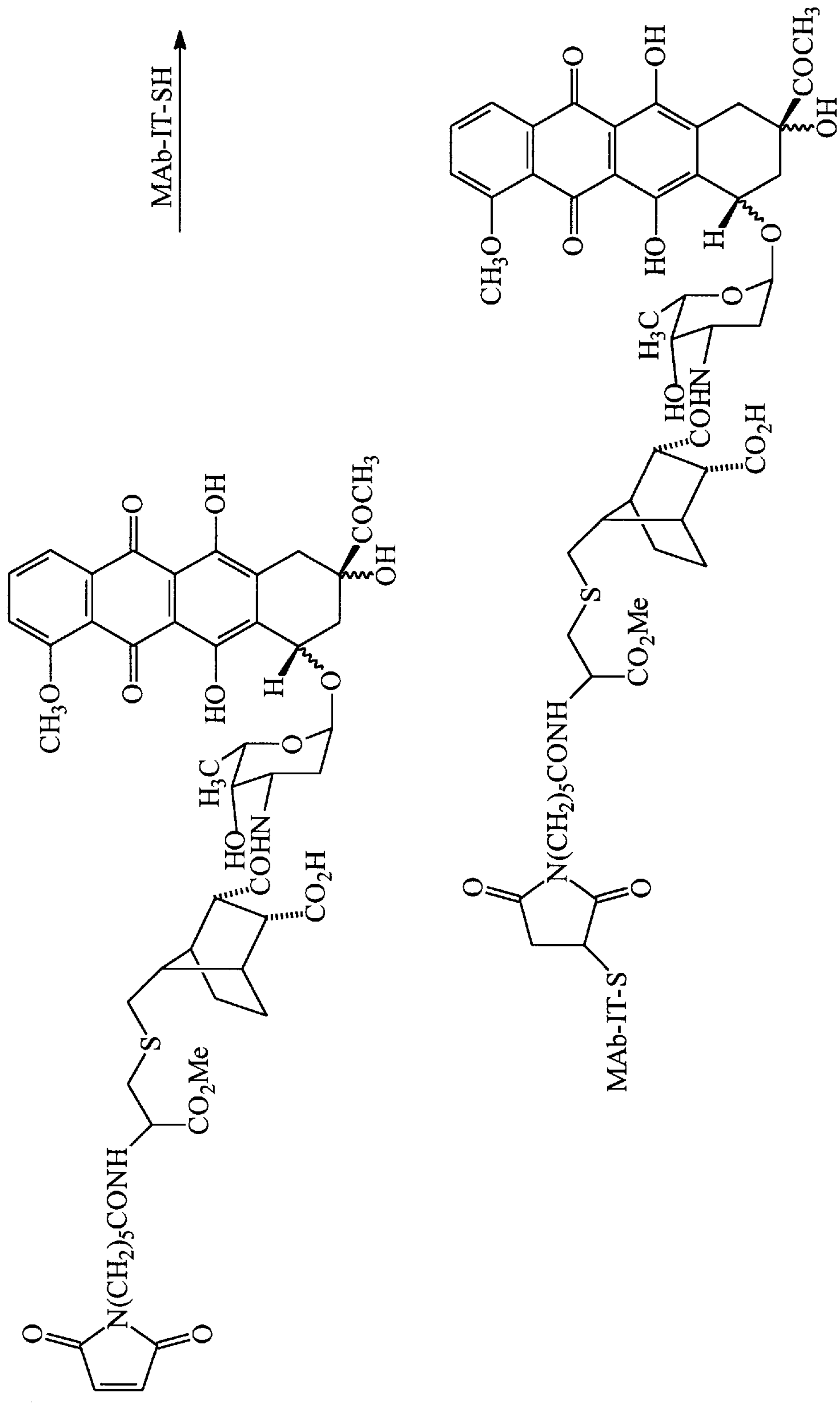
FIG. 7 outlines the reaction pathway described in Example 7.

This reaction scheme is summarized in FIG. 7.

Example 8

Formation of Targeting Substance Toxin Conjugate using Targeting Substance Sulfhydryls or Targeting Substance Lysines.

To a solution of the reduced MAb or the sulfhydryl-derivatized MAb in PBS, pH 6.5 (as prepared in Examples 6 or 7), is added a solution of linker-derivatized PE in PBS, pH 7.5 in the desired amount to achieve the desired level of derivatization of the MAb. The final pH is adjusted to pH 6.5 by the addition of 0.1 $NaH_2PO_4$. The reaction mixture is agitated at room temperature for the appropriate period of time. The MAb-linker-PE conjugate is purified from unreacted PE by FPLC (Pharmacia, Uppsala, Sweden) using a superose-12 column, eluting with PBS, pH 7.5.

Figure 8:
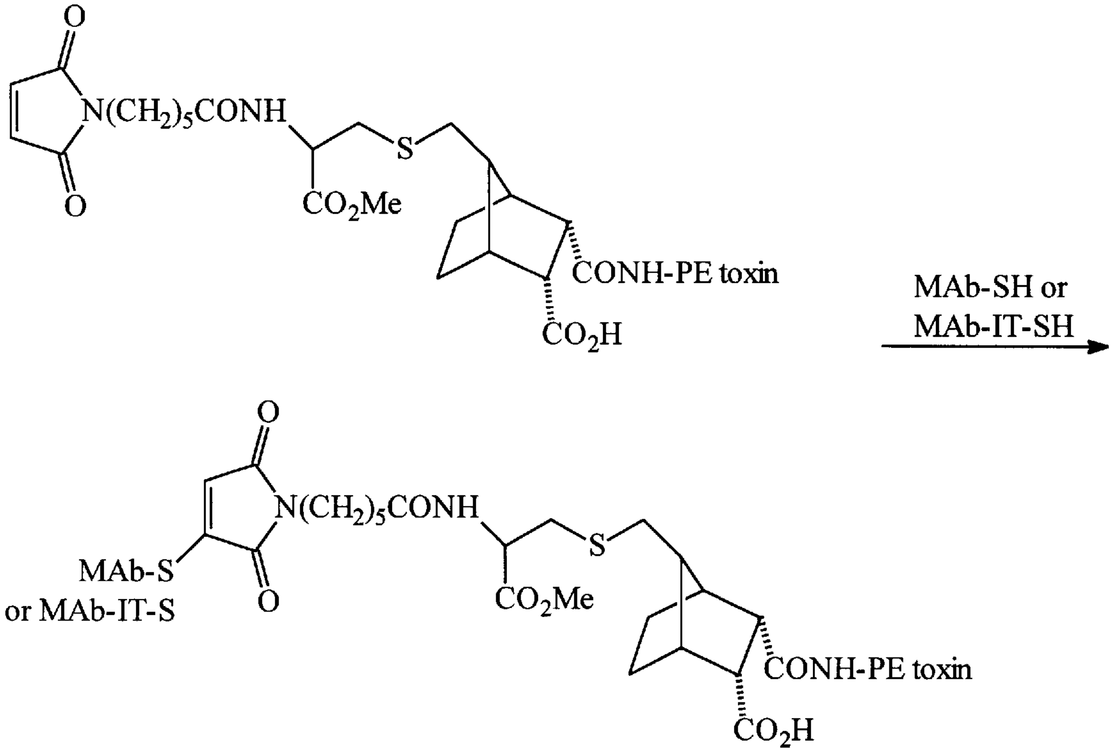
FIG. 8 outlines the reaction pathway described in Example 8.

This reaction scheme is summarized in FIG. 8.

Example 9

Synthesis of Linker 15.

The process for making the linker of Example 1 is followed, except that cyclopentadiene is replaced with cyclohexadiene in the Diels-Alder reaction with 2.

Figure 9:
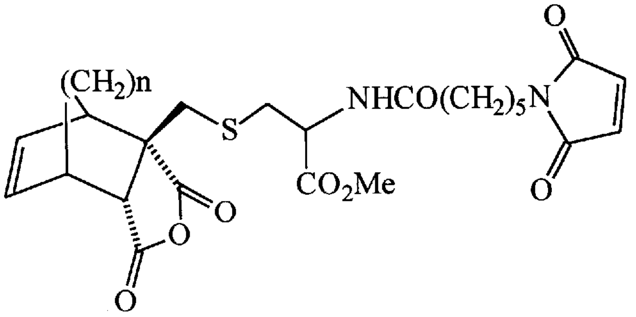
FIG. 9 shows the linkers produced by the reactions described in Examples 1, 9, 10, and 11.
Figure 9:
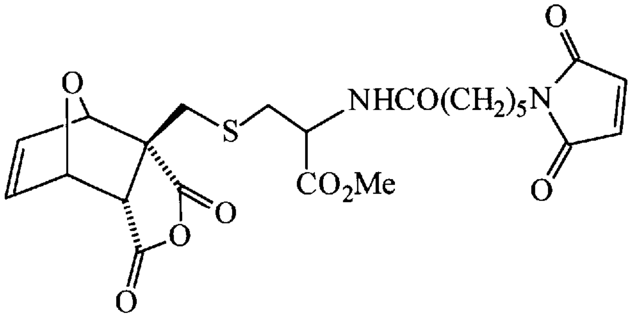

This compound is shown in FIG. 9.

Example 10

Synthesis of Linker 16.

The process for making the linker of Example 1 is followed, except that cyclopentadiene is replaced with cycloheptadiene in the Diels-Alder reaction with 2.

This compound is shown in FIG. 9.

Example 11

Synthesis of Linker 17.

The process for making the linker of Example 1 is followed, except that cyclopentadiene is replaced with furan in the Diels-Alder reaction with 2.

This compound is shown at the bottom of FIG. 9.

Example 12

Hydrolysis Kinetics of a Model Bicyclic Compound 18.

To determine the hydrolysis kinetics of a model bicyclic compound, it was placed into a 100 nM $NaP_i$ buffer in $D_2O$ and the kinetics were measured by NMR spectroscopy. Quantitation was made by successive integrations of one of the two NMe singlets of 18 and the NMe singlet of $Me_2NH$. First order rate constants were obtained at several different pDs. The data is shown in Table 2:

TABLE 2

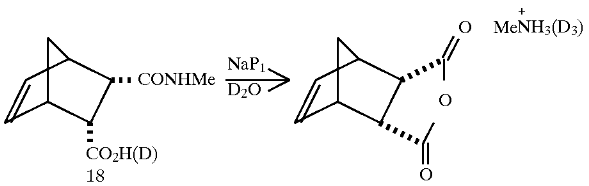

18

18

| pD | $T_{1/2}$ | k (sec − 1) |
|---|---|---|
| 8.57 | 262 hr | $7.34 \times 10^{-7}$ |
| 7.68 | 20.7 hr | $9.31 \times 10^{-6}$ |
| 7.00 | 136 min | $8.52 \times 10^{-5}$ |
| 6.70 | 91.4 min | $1.26 \times 10^{-4}$ |
| 6.39 | 49.4 min | $2.34 \times 10^{-4}$ |
| 5.99 | 5 min | $2.25 \times 10^{-3}$ (est) |
| 5.09 | 79 sec | $8.75 \times 10^{-3}$ (est) |

The $T_{1/2}$ measured at pD 5.09 is an estimate because the reaction is too fast to be accurately followed by NMR. The $T_{1/2}$ at pD 5.09 is extremely short (approximately 79 sec.) while the $T_{1/2}$ at pD 7.68 is 20.7 hrs. The $T_{1/2}$ at pD 5.09 is very well suited for the intended use. The hydrolysis kinetics of the [2.2.2] analogue should be slower than the [2.2.1] compound at the same pH since the equilibrium constant for anhydride formation in the parent diacid in water of the

[2.2.1]bicyclic system is greater than the [2.2.2]bicyclic system. There should be no significant difference in the $PK_a$ between the two analogues.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having the formula:

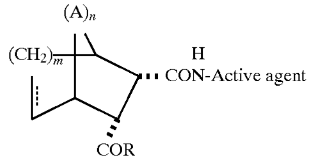

wherein:

A is $—CH_2—$, —O—, —S— or >N—$C_{1-6}$-alkyl, wherein n is 1, 2 or 3, when A is $—CH_2—$, or n is 1 when A is —O—, —S— or >N—$C_{1-6}$-alkyl;

m is 1 or 2;

-------- is a single or double bond; and

R is OH, $OR_1$, or $SR_1$, wherein $R_1$ is an ester moeity;

wherein the amino group from which the amido group is derived is from the active agent which istherapeutically or diagnostically active; and wherein the bicyclic ring is further substituted by a linker arm of 1–12 carbon atoms in length and having a reactive group effective for covalently linking to a peptide or protein which can direct the compound to a specific site.

2. A bicyclic, non-aromatic hydrocarbon compound having 7–10 carbon atoms and 0–1N, O or S atom in the bicyclic skeleton, and having as substituents an acid group and an amido group which are vicinal and in a syn-position, wherein the amido group is not anilido and the acid group is carboxyl or carboxyl in a form metabolizable to a free carboxyl group, and wherein said bicyclic skeleton is optionally unsaturated, except in the bond between said groups, wherein the bicyclic ring is further substituted by a linker arm of 1–12 carbon atoms in length and having a reactive group effective for linking to a peptide or protein which can direct the compound to a specific site.

3. A bicyclic compound of claim 1, wherein the linker arm is substituted at the carbon to which the amido or carboxyl group is attached.

4. A bicyclic compound of claim 1, wherein the linker arm is substituted at the A group.

5. A bicyclic compound of claim 1, wherein the linker arm is substituted at a carbon atom in a bicyclic ring.

6. A bicyclic compound of claim 1, wherein the linker arm is a functionalized cysteine as depicted in compound 6 of FIG. 1.

7. A bicyclic compound of claim 1, wherein the reactive group on the linker arm is capable of reacting with a sulfhydryl-containing group.

8. A bicyclic compound of claim 1, wherein the amido group can be released under mild acidic conditions of pH≥5.0 with a $T_{1/2}$ of about 8 hours or less.

9. A bicyclic, non-aromatic hydrocarbon compound having 7–10 carbon atoms and 0–1N, O or S atom in the bicyclic skeleton, and having as substitutents an acid group and an amido group which are vicinal and in a syn-position, wherein the acid group is carboxyl or carboxyl in a form metabolizable to a free carboxyl group, said bicyclic skeleton is optionally unsaturated except in the bond between said groups, the amido group is acid-cleavable, and the bicyclic ring is further substituted by a linker arm of 1–12 carbon atoms in length and having a reactive group effective for covalently linking to a peptide or protein which can direct the compound to a specific site.

10. A compound of claim 7, which is

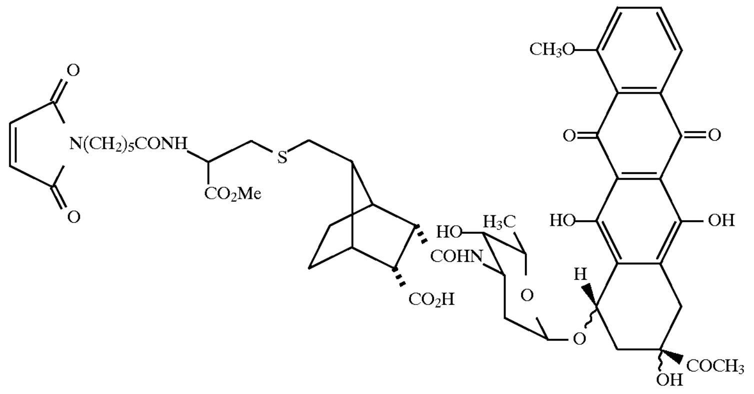

11. A compound of claim 9, wherein said bicyclic skeleton is unsaturated.

12. A compound of claim 1, wherein said linker arm is cysteine having a methylated carboxyl.

13. A compound of claim 9, wherein said reactive group on the linker arm is capable of reacting with a sulfhydryl group.

* * * * *